United States Patent [19]

Sakamoto et al.

[11] 4,416,891

[45] Nov. 22, 1983

[54] ESTER OF 6-[HEXAHYDRO-1H-AZEPIN-1-yl)METHYLENEAMINO]PENICILLANIC ACID, AND ITS USE AS ANTIBACTERIAL AGENT

[75] Inventors: Fumio Sakamoto, Osaka; Shoji Ikeda, Ibaraki; Goro Tsukamoto, Toyonaka, all of Japan

[73] Assignee: Kanebo Ltd., Tokyo, Japan

[21] Appl. No.: 399,132

[22] Filed: Jul. 16, 1982

[30] Foreign Application Priority Data

Jul. 18, 1981 [JP] Japan .................... 56-112508

[51] Int. Cl.³ ................. C07D 499/00; A61K 31/425
[52] U.S. Cl. ............................. 424/270; 260/245.2 R; 260/239.1; 542/420
[58] Field of Search ........................ 424/270; 542/420; 260/245.2 R, 239.1

[56] References Cited

U.S. PATENT DOCUMENTS 3,755,588  8/1973  Lund .................................. 424/271
3,957,764  5/1976  Lund .................................. 260/240
4,089,963  5/1978  Bamberg et al. .................... 424/270

FOREIGN PATENT DOCUMENTS 48-5794  1/1973  Japan .

OTHER PUBLICATIONS

Nature New Biology, vol. 236, pp. 135–137, 4-5-72.
Chemotherapy 21:146–166 (1975).
Code of Federal Regulations, 21, Food & Drugs, Parts 100 to 199, pp. 697–698, 4-1-78.

Primary Examiner—Nicholas S. Rizzo
Attorney, Agent, or Firm—Wenderoth, Lind & Ponack

[57] ABSTRACT (5-Methyl-2-oxo-1,3-dioxolen-4-yl)methyl 6-[(hexahydro-1H-azepin-1-yl)methyleneamino]penicillanate of the following formula (I)

or its pharmaceutically acceptable acid addition salt.

The compound is useful as an antibacterial agent and may be prepared by reacting (5-methyl-2-oxo-1,3-dioxolen-4-yl)-methyl 6-aminopenicillanate of the following formula (II)

or its acid addition salt with chloro-N,N-hexamethyleneformiminium chloride, and as required, converting the resulting compound to its pharmaceutically acceptable acid addition salt.

2 Claims, No Drawings

ESTER OF 6-[(HEXAHYDRO-1H-AZEPIN-1-YL)METHYLENEAMINO]PENICILLANIC ACID, AND ITS USE AS ANTIBACTERIAL AGENT

This invention relates to a novel ester of 6-[(hexahydro-1H-azepin-1yl)methyleneamino]penicillanic acid (Mecillinam), an effective synthetic penicillin, a process for its production, and its use as an antibacterial agent.

More specifically, this invention relates to a novel Mecillinam ester of the following formula

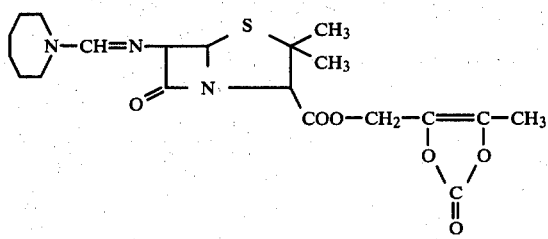

and its pharmaceutically acceptable acid addition salts, which are useful as a prodrug for oral administration of Mecillinam, a process for producing these compounds, and their use as an antibacterial agent.

Mecillinam represented by the following formula

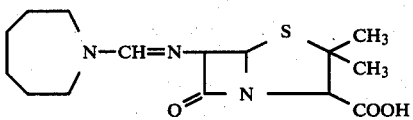

is a unique synthetic penicillin. In addition to its unique chemical structure based on the substituent at the 6-position, Mecillinam has the characteristic that in its antibacterial spectrum, it shows stronger activity against Gram-negative bacteria, especially *Escherichia coli* and *Klebsiella pneumoniae*, than against Gram-positive bacteria [see Nature New Biology, Vol. 236, 135-137 (1972)]. Mecillinam (X), however, has the defect that its absorbability or bioavailability in oral administration is low. For example, according to the paper of K. Roholt et al. [Chemotherapy, Vol. 21, 146-166 (1975)], pharmacokinetic studies of Mecillinam (X) by oral administration to man in a dose of 137 mg show that its maximum blood level is 0.19 μg/ml (an average of 6 cases) [cf. the minimum inhibitory concentration of Mecillinam (X) is generally 0.05 to 0.1 μg/ml or higher], and that its urinary excretion after the 6 hour period is as low as about 5%. Accordingly, the antibacterial activity of Mecillinam (X) cannot be fully utilized by oral administration.

In an attempt to remedy this defect of Mecillinam (X), its ester derivatives were studied, and the use of its pivaloyloxymethyl ester (Pivmecillinam) of the following formula

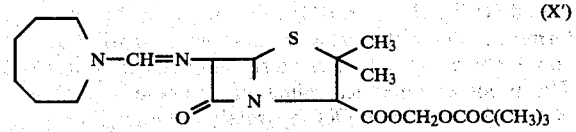

was suggested (see U.S. Pat. Nos. 3,755,588 and 3,957,764, and the paper of K. Roholt et al. cited above).

Pivmecillinam (X'), when administered orally, is rapidly absorbed in the body and readily undergoes hydrolysis in the body to give the parent compound, Mecillinam (X), in a high concentration. For example, the abve cited paper of K. Roholt et al. states that the maximum concentration of Mecillinam in the blood in the oral administration of 200 mg (137 mg as Mecillinam) of Pivmecillinam to man is 3.1 μg/ml (an average of 10 cases) which is more than 15 times as high as that obtained in oral administration of Mecillinam as mentioned above, and its urinary excretion after the 6 hour period is as high as 45% in a dose of 400 mg.

Accordingly, Pivmecillinam (X') is useful as a prodrug for oral administration of Mecillinam (X) and is now clinically used for this purpose.

It is said that Pivmecillinam (X') is transformed to Mecillinam (X) in accordance with the following mode of decomposition (see the paper of K. Roholt et al. cited above) in vivo.

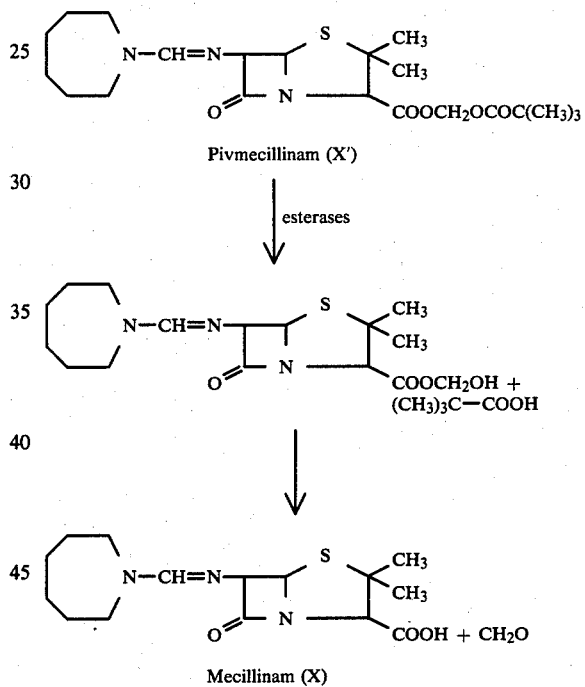

As is seen from the above scheme, formaldehyde is liberated during the transformation of Pivmecillinam to Mecillinam (X). Formaldehyde is detrimental to living organisms.

It is an object of this invention therefore to provide a novel Mecillinam ester.

Another object of this invention is to provide a novel Mecillinam ester useful as a prodrug for oral administration of Mecillinam (X).

Still another object of this invention is to provide a novel Mecillinam ester which has excellent absorbability or bioavailability in oral administration comparable to the known effective prodrug, Pivmecillinam (X'), and which is transformed in the body to Mecillinam (X) without forming a noxious decomposition product.

Yet another object of this invention is to provide a process for advantageously producing the aforesaid novel Mecillinam ester.

A further object of this invention is to provide an antibacterial agent comprising the novel Mecillinam ester as an active ingredient.

These objects of this invention are achieved by (5-methyl-2-oxo-1,3-dioxolen-4-yl)methyl 6-[(hexahydro-1H-azepin-1-yl)methyleneamino]penicillanate of the following formula (I) or its pharmaceutically acceptable acid addition salts.

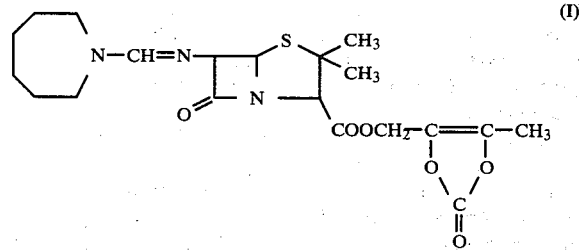

(I)

The pharmaceutically acceptable acid addition salts of the ester of formula (I) include, for example, its hydrochloride, sulfate, maleate and p-toluenesulfonate.

These compounds of the invention have been pharmacologically studied in vitro and in vivo, and found to be a useful and highly safe prodrug for oral administration of Mecillinam (X).

Firstly, stability tests of the compounds of this invention in artificial body fluids and in serum have led to the conclusion that these compounds are believed to be stable in gastric juice and intestinal juice, whereas they rapidly undergo hydrolysis in blood to form Mecillinam (X) (see Test Examples 1, 2 and 3 given hereinbelow). Secondly, it has been found that when the compounds of this invention are orally administered, they are easily absorbed and exhibit high antibacterial activity comparable to Pivmecillinam (X') in blood (see Test Example 4 given hereinbelow). Thirdly, it has been ascertained that the compounds of this invention have extremely low toxicity ($LD_{50}$) (see Test Example 5 given hereinbelow), and during their transformation to Mecillinam (X) in vivo, their ester residue

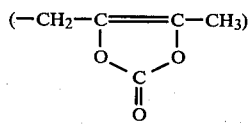

is converted to diacetyl as can be seen from the following scheme.

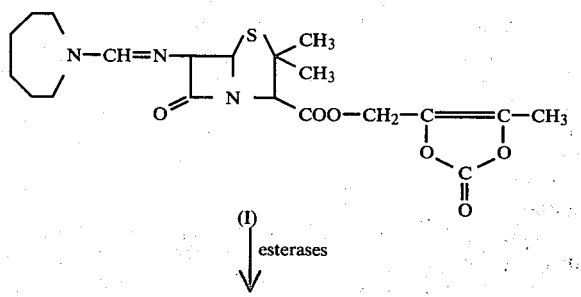

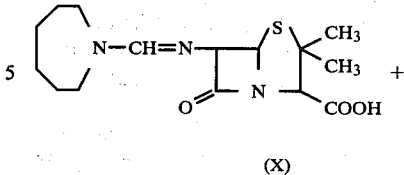

(X)

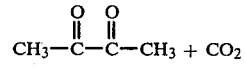

In view of the fact that the use of diacetyl as a food additive is approved (see Code of Federal Regulations, 21, Food and Drugs, Parts 100 to 199, pages 697–698), the compounds of this invention are believed to have high safety in administration for a long period of time or in large amounts.

These pharmacological tests are described below in detail.

TEST EXAMPLE 1

Stability in an artificial gastric juice (a) Test compound (5-methyl-2-oxo-1,3-dioxolen-4-yl)methyl 6-[(hexahydro-1H-azepin-1-yl)methleneamino]penicillanate hydrochloride monohydrate [compound (I).HCl.$H_2O$]

(b) Experimental procedure (1) Test solution

A solution of 2 mg of compound (I).HCl.$H_2O$ in 0.2 ml of dimethyl sulfoxide was added to 3.8 ml of the artificial gastric juice described in The Pharmacopoeia of Japan, 10th edition (having a pH of about 1.2 and prepared by adding 24.0 ml of 10% HCl to 2.0 g of sodium chloride and adding water to adjust the total amount to 1000 ml). The solution was maintained at 37° C., and bioautographed as shown below after the lapse of 10 minutes, 30 minutes, and 50 minutes, respectively.

(2) Bioautography (i) The test solution was spotted on a cellulose plate [Cellulose F (Art 5718 supplied by Merck & Co.)] for thin-layer chromatography, and developed with the upper layer of a mixture of n-butanol, ethanol and water in a ratio of 4:1:5. The plate was dried in the air, and a 10% aqueous solution of mouse serum was sprayed onto the plate. The plate was left to stand at 37° C. for 30 minutes and again dried in the air.

(ii) 0.2 ml of a suspension of *Escherichia coli* NIHJ as test organism (cell concentrations: $10^9$ cells/ml) was added to 5 ml of nutrient agar kept at about 48° C. to prepare an agar plate.

(iii) The thin-layer chromatographic plate prepared in (i) was kept in inititmate contact with the agar plate for 30 minutes. The thin-layer chromatographic plate was removed, and then the agar plate was maintained at 37° for 18 hours.

(iv) After the cultivation, the position (Rf value) of an inhibitory zone on the plate against *E. coli* NIHJ was determined. From this Rf value and Rf values of compound (I).HCl.$H_2O$ and Mecillinam (X) separately determined under the same conditions as in (i) to (iii) above, the compound in the test solution was identified. The predetermined Rf values of compound (I).HCl.$H_2O$ and Mecillinam (X) separately obtained were 0.9 and 0.5, respectively.

(c) Results

In any of the test solutions sampled 10, 30 and 50 minutes later, an inhibitory zone was observed only at an Rf of 0.9, and not at an Rf of 0.5. It is concluded therefore that the compound (I).HCl.H$_2$O is stable for a period of more than 50 minutes in the artificial gastric juice.

TEST EXAMPLE 2

Stability in an artificial intestinal juice (a) Test compound

Compound (I).HCl.H$_2$O.

(b) Experimental procedure (1) Test solution

A test solution was prepared in the same way as in Test Example 1, (b), (1) except that the artificial intestinal juice described in The Pharmacopoeia of Japan, 10th edition (having a pH of about 6.8 and prepared by adding water to 250 ml of a 0.2 M aqueous solution of potassium dihydrogen phosphate and 118 ml of a 0.2 N aqueous solution of sodium hydroxide to form a solution having a total volume of 1000 ml) was used instead of the artificial gastric juice.

(2) Bioautography

Performed in the same way as in Test Example 1, (b), (2).

(c) Results

In any of the test solutions examined, an inhibitory zone was observed only at an Rf of 0.9 as in Test Example 1. It was thus concluded that compound (I).HCl.H$_2$O is also stable in the artificial intestinal juice.

TEST EXAMPLE 3

Stability in mouse serum (a) Test compound

Compound (I).HCl.H$_2$O.

(b) Experimental procedure (1) Test solution 4 ml of mouse serum was added to 5.6 ml of 0.1 M phosphate buffer (pH 7.4), and then a portion (0.4 ml) of a solution of 20 mg of compound (I).HCl.H$_2$O in 1 ml of dimethyl sulfoxide was added. The solution was kept at 37° C. for 10 minutes to form a test solution.

(2) Bioautography

The test solution obtained in (1) above was subjected to the same operation as in Example 1, (b), (2).

(c) Results

An inhibitory zone was observed only at an Rf of 0.5, and not at an Rf of 0.9.

This led to the conclusion that compound (I).HCl.H$_2$O is transformed to Mecillinam (X) in 40% mouse serum within ten minutes at 37° C.

TEST EXAMPLE 4

Antibacterial activity in oral administration to mice (a) Test compounds

Compound (I).HCl.H$_2$O and Pivmecillinam.HCl.

(b) Experimental procedure (1) Experimental animals

Male ddY mice (6 weeks old, body weight 28±2 g) were used. They were caused to fast for 16 hours before the administration of the test compounds.

(2) Administration

An aqueous solution (5 mg/ml) of each of the test compounds was prepared, and orally administered to mice (five per group) in a dose corresponding to 50 mg/kg of Mecillinam.

(3) Blood letting

Blood samples were taken individually from five mice in each group at 30, 60 and 90 minutes after the administration of each compound. The blood samples were immediately centrifuged individually at 3,000 rpm for 15 minutes, and serum samples obtained (each in an amount of 0.2 ml) were combined to give 1 ml of serum for assaying.

(4) Measurement of antibacterial activity 0.2 ml of a suspension of *Escherichia coli* NIHJ as test organism was added to 5 ml of nutrient agar kept at about 48° C. to give an agar plate. The assaying serum prepared in (3) above was infiltrated into a paper disc (a thick type with a diameter of 8 mm, supplied by Toyo Filter Paper Co., Ltd.), and the paper disc was placed on the agar plate (n=4). It was maintained at 37° C. for 18 hours, and the diameter of the resulting inhibitory zone was measured with respect to each of the serum samples.

(c) Results

The diameter of the inhibitory zone (an average of n=4) measured with respect to each of the serum samples was as shown in Table 1.

TABLE 1

| | Diameter of the inhibitory zone (mm) | | |
|---|---|---|---|
| | Blood letting time (min.) | | |
| Test Compound | 30 | 60 | 90 |
| Compound (I).HCl.H$_2$O | 23.3 | 20.0 | 17.2 |
| Pivmecillinam.HCl | 23.2 | 20.8 | 18.0 |

TEST EXAMPLE 5

Toxicity test

The acute toxicity (LD$_{50}$) of compound (I).HCl.H$_2$O and Pivmecillinam.HCl in oral administration was examined by using male ddY-strain mice (body weight 22 to 25 g; five per group). The results are shown in Table 2.

TABLE 2

| Test Compound | LD$_{50}$(p.o.) mg/kg |
|---|---|
| Compound (I).HCl.H$_2$O | 5206 |
| Pivmecillinam.HCl | 3842 |

It is clear from the above results that the compounds of this invention can be an effective and safe prodrug for Mecillinam (X).

The compound of formula (I) and its pharmaceutically acceptable acid addition salts can be advantageously produced by a process which comprises reacting a 6-aminopenicillanic acid ester of the following formula (II)

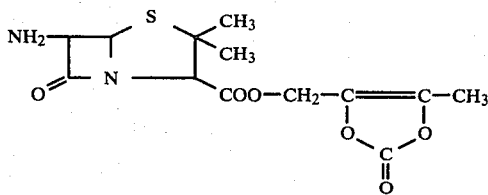

or its acid addition salt with chloro-N,N-hexamethyleneformiminium chloride of the following formula (III)

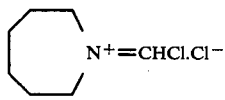

and as desired, converting the resulting compound to its pharmaceutically acceptable acid addition salt.

The 6-aminopenicillanic ester of formula (III) and its acid addition salt are produced by the action of a 4-halomethyl-5-methyl-1,3-dioxolen-2-one of the following formula (IV)

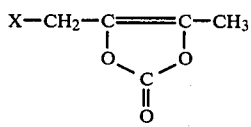

wherein X represents a halogen atom, on 6-aminopenicillanic acid or its salt preferably having its amino group protected by a trityl group.

The compound of formula (IV) is produced by reacting 5-methyl-1,3-dioxolen-2-one of the following formula (V)

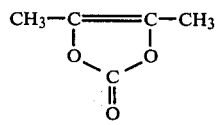

with a halogenating agent.

The compound of formula (V) is produced by the methods described in Tetrahedron Letters, No. 17, pages 1701–1704 (1972) and Transactions, Ill. State Acad. Sci., Vol. 67, No. 1, pages 139–144 (1974).

Examples of the halogenating agent for producing the compound of formula (IV) from the compound of formula (V) include N-bromo(or N-chloro)succinimide, N-bromo(or N-chloro)phthalimide, bromine, and chlorine. In order to perform the halogenation reaction favorably, an equimolar or slightly excessive proportion of the halogenating agent is used relative to the compound (V), and these materials are reacted in an inert solvent such as methylene chloride, carbon tetrachloride or benzene at a temperature ranging from room temperature to the boiling point of the solvent. Preferably, a radical initiator such as $\alpha,\alpha'$-azobisisobutyronitrile is used, or radicals are generated by ultraviolet light exposure.

A compound of formula (IV) in which X is an iodine atom is produced by a known halogen-substitution reaction involving the action of sodium iodide, for example, on a compound of formula (IV) in which X is a bromine atom.

The 6-aminopenicillanic acid ester of formula (II) is prepared from 6-aminopenicillanic acid or its salt (preferably having its amino group protected by a trityl group) and the compound (IV). The compound (IV) is used in an equimolar or slightly excessive proportion relative to 6-aminopenicillanic acid or its metal salt in which the amino group is preferably protected by a trityl group, etc. These compounds are reacted at room temperature or under ice cooling in an inert organic solvent such as ethyl acetate, tetrahydrofuran, dioxane, acetone, dimethylformamide, or dimethyl sulfoxide preferably in the presence of a base such as trialkylamines, alkali bicarbonates, and alkali carbonates. When 6-aminopenicillanic acid with its amino group protected by a trityl group, or its salt is used, the resulting product is deprotected in a customary manner. Preferably, the 6-aminopenicillanic acid ester (II) is isolated as its acid addition salt.

Finally, the ester (I) or its pharmaceutically acceptable acid addition salt in accordance with this invention is produced in the following manner from the 6-aminopenicillanic acid ester (II) or its acid addition salt and chloro-N,N-hexamethyleneformiminium chloride (III). The reaction of the compound (II) or its acid addition salt with the compound (III) is carried out in an inert organic solvent in the presence of a base. The compound (II) or its acid addition salt and the compound (III) are used preferably in equimolar proportions. Preferably, chloroform, dichloromethane and carbon tetrachloride are used as the inert organic solvent. The base is, for example, a trialkylamine. The reaction is carried out preferably at −40° to 5° C., especially −10° to 0° C. for 1 to 3 hours. Furthermore, the resulting ester (I) can be converted to its pharmaceutically acceptable acid addition salt by treating it with a corresponding acid.

The ester of formula (I) or its acid addition salt can also be produced by reaction of Mecillinam (X) with the compound (IV).

For use as a prodrug, the compound of this invention is administered to a warm-blooded animal, preferably man, preferably in the form of its pharmaceutically acceptable acid addition salt and preferably by oral administration. The dose of this compound is usually in the range of 50 to 1,000 mg per day for a human adult. It can be administered once or in 2 to 4 divided portions a day. It can be administered in dosage forms such as pellets, granules, tablets, capsules, etc. prepared in a customary manner by using conventional drug additives such as starch, lactose, hydroxypropyl cellulose, crystalline cellulose, and magnesium stearate.

The following Examples illustrate the present invention in greater detail.

EXAMPLE 1

Production of (5-methyl-2-oxo-1,3-dioxolen-4-yl)methyl 6-[(hexahydro-1H-azepin-1-yl)methyleneamine]-penicilanate hydrochloride [hydrochloride of compound of formula (I)]

(1) Production of 4-bromomethyl-5-methyl-1,3-dioxolen-2-one [compound of formula (IV) wherein X is a bromine atom]

3.42 g of 4,5-dimethyl-1,3-dioxolen-2-one [synthesized in accordance with the method disclosed in Tetrahedron Letters, Vol. 17, pages 1701-1704 (1972)] was dissolved in 150 ml of carbon tetrachloride, and 5.34 g of N-bromosuccimide and a catalytic amount of α,α'-azobisisobutyronitrile were added. The mixture was refluxed for 15 minutes. The reaction mixture was concentrated to one-half of its original volume, and insoluble materials were removed by filtration. The filtrate was concentrated. The resulting syrupy residue was distilled under reduced pressure. A fraction boiling at 115°-120° C./5 mmHg was collected, and 4.2 g of the captioned compound was obtained as a colorless liquid in a yield of 73%.

Elemental analysis for $C_5H_5BrO_3$:

|  | C | H | Br |
| --- | --- | --- | --- |
| Calculated (%) | 31.12 | 2.61 | 41.40 |
| Found (%) | 31.30 | 2.49 | 41.31 |

IR (neat, $\nu$ cm$^{-1}$): near 1825 (carbonyl).

NMR (CCl$_4$, δ ppm): 2.10 (—CH$_3$, s), 4.10 (—CH$_2$Br, s).

(2) Production of (5-methyl-2-oxo-1,3-dioxolen-4-yl)methyl 6-aminopenicillanate p-toluenesulfonate [p-toluenesulfonate of the compound of formula (II)]

13 g of 6β-tritylaminopenicillanic acid [synthesized in accordance with the method described in J. Am. Chem. Soc., Vol. 84, page 2983 (1963)] was dissolved in 100 ml of dimethylformamide. The solution was cooled to 0°-5° C., and 3 g of potassium bicarbonate and 6 g of the 4-bromomethyl-5-methyl-1,3-dioxolen-2-one obtained in (1) above were added. The mixture was stirred at the same temperature for 3 hours. After the reaction, the reaction mixture was poured into ice water. The solid which precipitated was extracted with ethyl acetate. The ethyl acetate layer was washed several times with a saturated aqueous solution of sodium chloride, dried over anhydrous magnesium sulfate, and concentrated under reduced pressure to give a yellow syrup. The syrup was dissolved in 80 ml of ethyl acetate, and with ice cooling, 5.2 g of p-toluenesulfonic acid was added. When the mixture was stirred for 1 hour with ice cooling, a colorless solid precipitated. The solid was collected by filtration, and washed well with a mixture of ethyl acetate and ether (1:1) to give 8.3 g of the captioned compound in a yield of 60%.

Melting point: 130°-138° C. (decomp.).

Elemental analysis for $C_{13}H_{16}N_2O_6S \cdot CH_3C_6H_4SO_3H$:

|  | C | H | N |
| --- | --- | --- | --- |
| Calculated (%) | 47.99 | 4.83 | 5.60 |
| Found (%) | 47.31 | 4.82 | 6.00 |

IR (KBr, $\nu$ cm$^{-1}$): 1820 (cyclic carbonate), 1780 (β-lactam), 1760 (ester).

NMR (DMSO-d$_6$, δ ppm): 1.40, 1.59 (6H, methyl at 2-position, s), 2,12

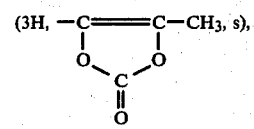
(3H, —C═C—CH$_3$, s), 4.46 (1H, proton at 3-position, s), 4.90–5.10

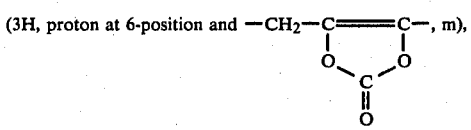
(3H, proton at 6-position and —CH$_2$—C═C—, m), 5.41 (1H, proton at 5-position, d), 2,24

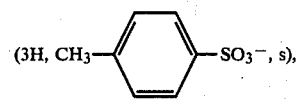
(3H, CH$_3$—⟨⟩—SO$_3^-$, s), 6.97, 7.38

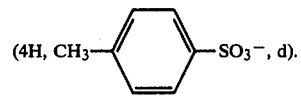
(4H, CH$_3$—⟨⟩—SO$_3^-$, d).

(3) Production of (5-methyl-2-oxo-1,3-dioxolen-4-yl)methyl 6-[(hexahydro-1H-azepin-1-yl)methyleneamino]penicillanate hydrochloride [hydrochloride of the compound of formula (I)]

2.5 g of the (5-methyl-2-oxo-1,3-dioxolen-4-yl)methyl 6-aminopenicillanate p-toluenesulfonate obtained in (2) above was suspended in 150 ml of ethyl acetate, and 100 ml of a 2% aqueous solution of sodium bicarbonate cooled at 0° C. was added. The mixture was vigorously stirred. The ethyl acetate layer was then separated, washed with ice water, dried over anhydrous magnesium sulfate at 0° C., and concentrated under reduced pressure to give a pale yellow syrup. The syrup was dissolved in 20 ml of methylene chloride. Triethylamine (1.2 g) was added, and the solution was cooled at −20° C. A solution of 0.95 g of chloro-N,N-hexamethyleneformiminium chloride in 5 ml of methylene chloride was added dropwise slowly at the same temperature. The mixture was stirred at the same temperature for 1 hour, and the reaction mixture was concentrated under reduced pressure. Ethyl acetate (60 ml) was added to the resulting residue, and insoluble materials were removed by filtration. The ethyl acetate solution was washed with a 5% aqueous solution of sodium chloride, and then 80 ml of cold water was added. With stirring under ice cooling, the pH of the aqueous layer was adjusted to 2 with 1 N hydrochloric acid. The aqueous layer was separated, and sodium chloride was added to saturation. The resulting oily product was extracted with two 40 ml lots of methylene chloride. The methylene chloride layers were combined, washed with a 5% aqueous solution of sodium chloride, dried over anhydrous sodium sulfate, and concentrated under reduced pressure. The resulting syrup was treated with acetone-ether to give 0.9 g of the captioned compound as a pale yellow solid in a yield of 30%.

Melting point: It began to melt at about 100° C. and became tarry at about 140° C.

Elemental analysis for $C_{20}H_{27}N_3O_6S \cdot HCl \cdot H_2O$:

|  | C | H | N |
|---|---|---|---|
| Calculated (%) | 48.83 | 6.14 | 8.52 |
| Found (%) | 48.92 | 6.21 | 8.26 |

IR (KBr, $\nu$ cm$^{-1}$): 1825, 1790, 1755 (carbonyl), 1690 (C=N—).

NMR (CDCl$_3$, $\delta$ ppm): 1.5–2.1

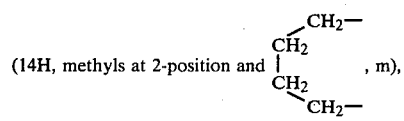

(14H, methyls at 2-position and ..., m),

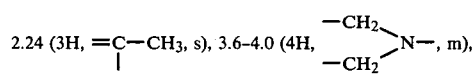

2.24 (3H, =C—CH$_3$, s), 3.6–4.0 (4H, ..., m), 4.52 (1H, proton at 3-position, s),

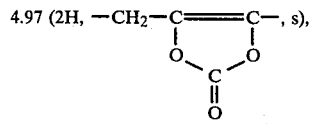

4.97 (2H, —CH$_2$—C=C—, s), 5.56–5.68 (2H, protons at 5- and 6-positions, m), 7.87 (1H, —N—CH=N—, s).

EXAMPLE 2

Production of (5-methyl-2-oxo-1,3-dioxolen-4-yl)methyl 6-[(hexahydro-1H-azepin-1yl)methyleneamino]penicillanate [compound of formula (I)]

One gram of (5-methyl-2-oxo-1,3-dioxolen-4-yl)methyl 6-[(hexahydro-1H-azepin-1yl)methylenamino]penicillanate hydrochloride monohydrate was dissolved in 15 ml of water, and 20 ml of ethyl acetate was added. With stirring at 0° C., the pH of the mixture was adjusted to 7.6 with a 10% aqueous solution of sodium bicarbonate. The ethyl acetate was separated, washed with a saturated aqueous solution of sodium chloride, and dried over anhydrous magnesium sulfate, and ethyl acetate was evaporated under reduced pressure to give 0.7 g of the captioned compound as a pale yellow syrup in a yield of 79%.

IR (neat, $\nu$ cm$^{-1}$): 1830, 1780, 1760 (carbonyl), 1640 (—CH=N—).

NMR (CDCl$_3$, $\delta$ ppm): 1.4–1.8

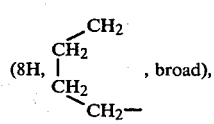

1.45 (3H, methyl at the 2-position, s), 1.67 (3H, methyl at the 2-position, s), 2.21

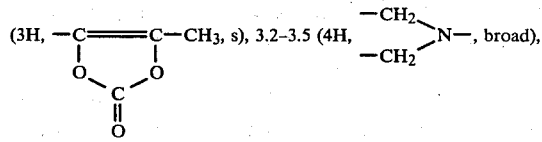

(3H, —C=C—CH$_3$, s), 3.2–3.5 (4H, ..., broad), 4.37 (1H, proton at the 3-position, s),

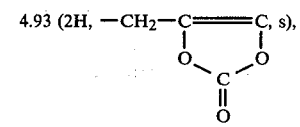

4.93 (2H, —CH$_2$—C=C, s), 5.10 (1H, proton at the 6-position, d, J=5 Hz), 5.46 (1H, proton at the 5-position, d, J=5 Hz), 7.60 (1H, —N—CH=N—, s).

EXAMPLE 3

Preparation of drugs (1) Capsules
Formulation:

| | |
|---|---|
| (5-Methyl-2-oxo-1,3-dioxolen-4-yl)methyl 6-[(hexahydro-1H—azepin-1-yl)methylamino)penicillanate hydrochloride monohydrate [compound (I).HCl.H$_2$O] | 750 parts by weight |
| Lactose | 235 parts by weight |
| Magnesium stearate | 15 parts by weight |
| | 1,000 parts by weight |

Procedure:

The above ingredients were mixed and encapsulated to form capsules. Each capsule contained 150 mg of compound (I).HCl.H$_2$O as an active ingredient.

(2) Granules
Formulation:

| | |
|---|---|
| Compound (I).HCl.H$_2$O | 300 parts by weight |
| Lactose | 670 parts by weight |
| Hydroxypropyl cellulose | 30 parts by weight |
| | 1,000 parts by weight |

An ethanol solution of hydroxylpropyl cellulose was prepared and added to compound (I).HCl.H$_2$O and lactose. They were kneaded, extruded through a screen and dried to form granules.

(3) Tablets
Formulation:

| | |
|---|---|
| Compound (I).HCl.H$_2$O | 600 parts by weight |
| Crystalline cellulose | 280 parts by weight |
| Lactose | 80 parts by weight |
| Hydroxypropyl cellulose | 28 parts by weight |
| Magnesium stearate | 12 parts by weight |
| | 1,000 parts by weight |

Procedure:

Compound (I).HCl.H$_2$O, crystalline cellulose and lactose were mixed, and an ethanol solution of hydroxypropyl cellulose was added. They were kneaded and dried. Magnesium stearate was added to the dried mixture. They were mixed and tabulated to form tablets. Each tablet contained 150 mg of compound (I).HCl.H$_2$O as an active ingredient.

What we claim is:

1. (5-Methyl-2-oxo-1,3-dioxolen-4-yl)methyl 6-[(hexahydro-1H-azepin-1-yl)methyleneamino]penicillanate of the following formula (I)

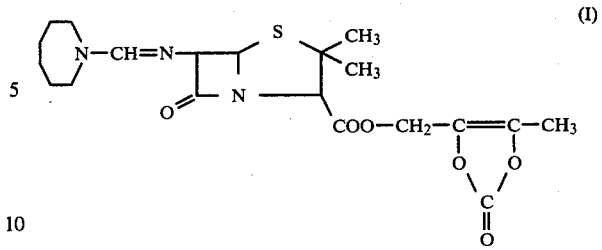

or a pharmaceutically acceptable acid addition salt thereof.

2. An antibacterial agent comprising an antibacterially effective amount of (5-methyl-2-oxo-1,3-dioxolen-4-yl)methyl 6-[(hexahydro-1H-azepin-1-yl)methyleneamino]penicillanate or a pharmaceutically acceptable acid addition salt thereof in association with a pharmaceutically acceptable carrier.

* * * * *